United States Patent

Shimizu et al.

[11] Patent Number: 5,155,106
[45] Date of Patent: Oct. 13, 1992

[54] CYSTEAMINE DERIVATIVES AND ANTIRHEUMATIC AGENTS CONTAINING CYSTEAMINE DERIVATIVES

[75] Inventors: Masaki Shimizu; Shingo Koyama; Hiromasa Kohama; Ryoichi Nanba; Kazuhito Inoue, all of Tokyo, Japan

[73] Assignee: Terumo Kabushiki Kaisha, Tokyo, Japan

[21] Appl. No.: 548,882

[22] PCT Filed: Jan. 19, 1989

[86] PCT No.: PCT/JP89/00044
§ 371 Date: Jul. 20, 1990
§ 102(e) Date: Jul. 20, 1990

[87] PCT Pub. No.: WO89/06648
PCT Pub. Date: Jul. 27, 1989

[30] Foreign Application Priority Data

Jan. 22, 1988 [JP] Japan .................................. 63-12154

[51] Int. Cl.⁵ .................. C07D 277/06; A61K 31/425
[52] U.S. Cl. ..................... 514/227.5; 514/365; 514/371; 514/438; 514/622; 544/58.4; 548/195; 548/200; 549/77; 564/177
[58] Field of Search .......... 564/177; 544/58.4; 548/200, 195; 549/77; 514/365, 371, 227.5, 438, 622

[56] References Cited

U.S. PATENT DOCUMENTS 3,455,940 7/1969 Stecker ........................... 514/365
3,917,617 11/1975 Razdan et al. .................. 514/365
3,985,891 10/1976 Kutter ............................. 546/48

FOREIGN PATENT DOCUMENTS 51819 5/1982 European Pat. Off. .
0001947 5/1979 PCT Int'l Appl. .

OTHER PUBLICATIONS

Chemical Abstracts 82(1) 4251y RN 53930-87-3.

Primary Examiner—Robert Gerstl
Attorney, Agent, or Firm—Burns, Doane, Swecker & Mathis

[57] ABSTRACT

A cysteamine derivative represented by general formula (I):

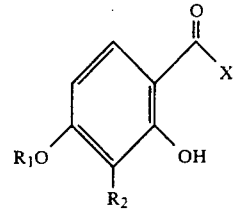

wherein $R_1$ represents a straight-chain or a branched alkyl radical having 1 to 6 carbon atoms, $R_2$ represents hydrogen atom or n-propyl radical, and X represents a radical selected from the group consisting of radicals containing cysteamine moiety (N/\/S) represented by formula (II):

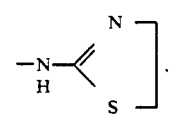

formula (III):

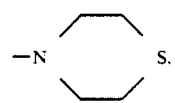

formula (IV):

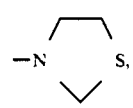

formula (V):

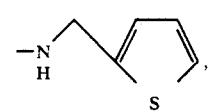

or
formula (VI):

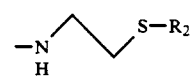

wherein $R_2$ represents hydrogen atom or a straight-chain or a branched alkyl group having 1 to 10 carbon atoms is provided.

The cysteamine derivative is effective as an antirheumatic agent.

18 Claims, No Drawings

CYSTEAMINE DERIVATIVES AND ANTIRHEUMATIC AGENTS CONTAINING CYSTEAMINE DERIVATIVES

TECHNICAL FIELD

The present invention relates to a novel cysteamine derivative and an antirheumatic agent containing the novel cysteamine derivative.

BACKGROUND ART

Steroids, acidic anti-inflammatory agents, and the like have been used for the therapy of rheumatism.

DISCLOSURE OF THE INVENTION

Steroids, however, involve various undesirable side-effects, and acidic anti-inflammatory agents remain nosotropic. Accordingly, there is a strong demand for a truly effective therapeutic agent.

The inventors of the present invention synthesized various cysteamine derivatives, extensively studied their physiological activities, and found that the cysteamine derivative in accordance with the present invention suppresses adjuvant arthritis, which is an animal experimental model for the rheumatism, to complete the present invention.

Therefore, an object of the present invention is to provide a novel cysteamine derivative and an antirheumatic agent containing such a cysteamine derivative.

The present invention, which accomplishes the aforesaid object, provides a cysteamine derivative represented by general formula (I):

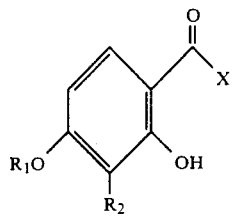

(I)

wherein $R_1$ represents a straight-chain or a branched alkyl radical having 1 to 6 carbon atoms, $R_2$ represents hydrogen atom or n-propyl radical, and X represents a radical selected from the group consisting of radicals containing cysteamine moiety (N∧S) represented by formula (II):

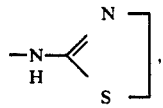

(II)

formula (III):

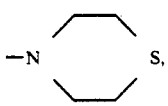

(III)

formula (IV):

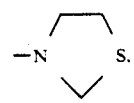

(IV)

formula (V):

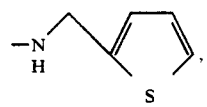

(V)

or formula (VI):

(VI)

wherein $R_2$ represents hydrogen atom or a straight-chain or a branched alkyl group having 1 to 10 carbon atoms.

The present invention also provides an antirheumatic agent containing a cysteamine derivative represented by general formula (I):

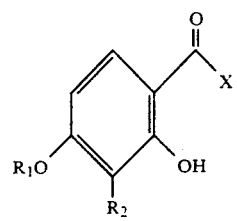

(I)

wherein $R_1$ represents a straight-chain or a branched alkyl radical having 1 to 6 carbon atoms, $R_2$ represents hydrogen atom or n-propyl radical, and X represents a radical selected from the group consisting of radicals containing cysteamine moiety (N∧S) represented by formula (II):

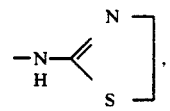

(II)

formula (III):

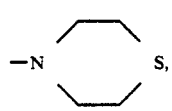

(III)

formula (IV):

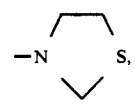

(IV)

formula (V):

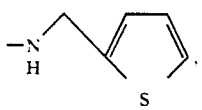

or
formula (VI):

wherein $R_2$ represents hydrogen atom or a straight-chain or a branched alkyl group having 1 to 10 carbon atoms.

The cysteamine derivative in accordance with the present invention which is represented by the above-mentioned formula (I) is produced by a condensation reaction and a protective group-removing reaction between a derivative of a carboxylic acid represented by the following formula (VII):

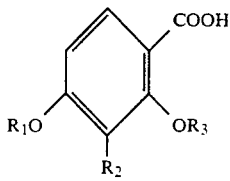

wherein $R_1$ represents a straight-chain or a branched alkyl group containing 1 to 6 carbon atoms, $R_2$ represents hydrogen atom or n-propyl group, and $R_3$ represents hydrogen atom or methoxymethyl group and an amine derivative represented by the following formula (VIII):

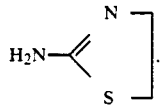

formula (IX):

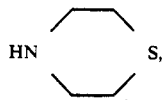

formula (X):

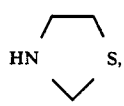

formula (XI):

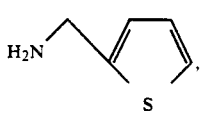

or formula (XIII)

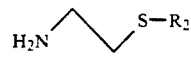

wherein $R_2$ represents hydrogen atom or a straight-chain or a branched alkyl group having 1 to 10 carbon atoms.

The cysteamine derivative of the present invention is used particularly for an antirheumatic agent, and is administered in a dose ranging from 10 to 2,000 mg per day, preferably from 20 to 600 mg per day in the case of an adult, although the dose may vary in accordance with the symptom. Such a dose of the antirheumatic agent is administered either at once or in two or three times a day as desired in accordance with the symptom. The administration may be carried out by any suitable method, and preferably, by oral administration. Intravenous injection may also be employed.

The compound of the present invention is employed either alone or as a mixture with another pharmaceutical carrier or vehicle as the only effective component or as one of effective components to form tablets, sugar-coating tablets, powders, capsules, granules, suspensions, emulsions, injections, and other pharmaceutical preparations. Examples of the carriers and vehicles include calcium carbonate, calcium phosphate, starch, glucose, lactose, dextrin, alginic acid, mannitol, talc, and magnesium stearate.

BEST MODE FOR CARRYING OUT THE INVENTION

Next, the present invention is described in further detail by referring to non-limiting Examples and Experiments.

EXAMPLE 1

12.05 g of 4-methoxysalicylic acid was dispersed in 200 ml of methylene chloride in argon atmosphere. To the dispersion were added 27.70 g of N,N-diisopropylethylamine and 19.20 g of chloromethylmethyl ether, and the mixture was agitated for 42 hours. The reaction mixture was poured into water, and extracted with methylene chloride. The extract was dried over anhydrous sodium sulfate. The solvent was distilled off in evacuated atmosphere, and 300 ml of methanol was added to the residue. To the mixture was added a solution which has been prepared by dissolving 8.50 g of sodium hydroxide in 20 ml of water. The mixture was agitated for 20 hours, neutralized with 6N aqueous hydrochloric acid, and the solvent was distilled off in evacuated atmosphere. The mixture was adjusted to pH 1 with 1N aqueous hydrochloric acid, and extracted with ethyl acetate. The extract was dried over anhydrous sodium sulfate, and the solvent was distilled off in evacuated atmosphere to produce 15 g of 4-methoxy-2-methoxy benzoic acid. To the product were added 8.50 g of 2-mercaptothiazoline, 15.34 g of N,'N-dicyclohexylcarbodiimide, 0.86 g of 4-dimethylaminopyridine, and 400 ml of 1,2-dichloroethane, and the mixture was agitated for 18 hours. The reaction mixture was filtered and the precipitate was washed with benzene. The filtrate and the wash liquid were combined, washed with 2N aqueous solution of sodium hydroxide, water, and saturated aqueous solution of sodium chloride in this order, and dried over anhydrous sodium sulfate. The solvent was distilled off in evacuated atomsphere, and the residue was subjected to a column chromatography using silica gel. There was obtained 12.36 g of N-(4-methoxy-2-methoxymethoxybenzoyl)thiazolidine-2-thion from fractions eluted with methylene chloride.

12.36 g of the thus produced N-(4-methoxy-2-methoxymethoxybenzoyl)thiazolidine-2-thion and 8.36 g of 2-aminothiazoline was dissolved in 150 ml of tetrahydrofuran, and the solution was agitated for 20 hours. To the solution was added 2N aqueous solution of sodium hydroxide. The mixture was extracted with methylene chloride and the extract was dried over anhydrous sodium sulfate. The solvent was distilled off in evacuated atmosphere, and the residue was subjected to column chromatography using silica gel. There was obtained 10.15 g of 2-(4-methoxy-2-methoxymethoxybenzoylamino)thiazoline from fractions eluted with methylene chloride.

To 8.87 g of the thus produced 2-(4-methoxy-2-methoxymethoxybenzoylamino)thiazoline was added 200 ml of aqueous hydrochloric acid-methanol, and the mixture was heated under reflux for 15 minutes. The solvent was distilled off in evacuated atmosphere, and to the residue was added saturated aqueous solution of sodium bicarbonate. The mixture was extracted with chloroform, and the extract was dried over anhydrous sodium sulfate. The solvent was distilled off in evacuated atmosphere and the residue was recrystallized from benzene to produce 6.39 g of 2-(2-hydroxy-4-methoxybenzoylamino)thiazoline.

Data obtained from spectroscopic analysis of the product confirm the structure represented by the following formula (XIII).

NMR (CDCl$_3$+CD$_3$OD)δ:
7.85 (1H, m)
6.35 (2H, m)
3.80 (3H, s)
4.00-3.10 (4H, m)

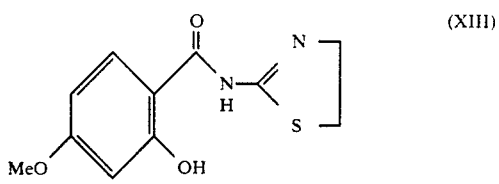

(XIII)

EXAMPLE 2

In argon atmosphere, a solution of potassium t-buthoxide (18.7 g) in tetrahydrofuran (200 ml) was cooled to 0° C., and to this solution was added dropwise a solution of methyl 2-hydroxy-3-n-propyl-4-methoxybenzoate (28 g) in tetrahydrofuran (100 ml) in 10 minutes, and the mixture was agitated for another 20 minutes. Chloromethyl ether (19.0 ml) was added thereto, and the mixture was agitated at 0° C. for 50 minutes. The reaction mixture was poured into 1N aqueous hydrochloric acid, and extracted twice with ethyl acetate. The organic layer was washed with saturated sodium bicarbonate, dried over anhydrous magnesium sulfate, and then concentrated in evacuated atmosphere. The residue was subjected to column chromatography using silica gel, and there was obtained methyl 2-methoxymethoxy-3-n-propyl-4-methoxybenzoate (29.9 g) from fractions eluted with n-hexane-ethyl acetate (10:1 to 5:1).

The methyl 2-methoxymethoxy-3-n-propyl-4-methoxybenzoate (31.9 g) was dissolved in methanol (280 ml), and 10% aqueous solution of sodium hydroxide (70 ml) was added thereto. The mixture was agitated at 60° C. for 4 hours and then at room temperature for another 80 hours. The reaction mixture was concentrated to about one third of the original volume in evacuated atmosphere, cooled to 0° C., acidified by adding 2N aqueous hydrochloric acid thereto, and then extracted twice with ethyl acetate. The organic layer was washed with saturated aqueous solution of sodium chloride, dried over anhydrous magnesium sulfate, and concentrated in evacuated atmosphere to produce 2-methoxymethoxy-3-n-propyl-4-methoxybenzoic acid (28.8 g).

Under argon atmosphere, a solution of 2-methoxymethoxy-3-n-propyl-4-methoxybenzoic acid (8 g) and 4-dimethylaminopyridine (0.38 g) in methylene chloride (150 ml) was cooled to 0° C., and to the solution was added N,N'-dicyclohexylcarbodiimide (7.8 g). The mixture was agitated for 15 minutes. Thiomorpholine (2.8 ml) was added to the mixture, and the mixture was agitated at room temperature for another 15 hours. To the reaction mixture was added diethyl ether, and the mixture was filtered. Water and 1N aqueous hydrochloric acid were added to the filtrate, and the mixture was extracted with methylene chloride. The organic layer was washed with saturated aqueous solution of sodium bicarbonate, dried over anhydrous magnesium sulfate, and concentrated in evacuated atmosphere. The residue was subjected to column chromatography using silica gel. There was obtained N-(2-methoxymethoxy-3-n-propyl-4-methoxybenzoyl)thiomorphorine (9.4 g) from fractions eluted with n-hexane-ethyl acetate (3:1 to 2:1).

The N-(2-methoxymethoxy-3-n-propyl-4-methoxybenzoyl)thiomorphorine (9.4 g) was dissolved in a solution of methanol (100 ml)-water (20 ml). To the solution was added p-toluenesulfonic acid (2 spoonfuls in spatula) and the mixture was agitated at 60° C. for 23 hours. The reaction mixture was concentrated in evacuated atmosphere to about one fourth of the original volume. Saturated aqueous solution of sodium bicarbonate was added to the concentrate, and the mixture was extracted twice with ethyl acetate. The organic layer was washed with saturated aqueous solution of sodium chloride, dried over anhydrous magnesium sulfate, and concentrated in evacuated atmosphere. The residue was recrystallized from methanol (50 ml) to obtain N-(2-hydroxy-3-n-propyl-4-methoxybenzoyl)thiomorpholine (4.5 g).

Data obtained from spectroscopic analysis of the product confirm the structure represented by the following formula (XIV).

NMR (CDCl$_3$)δ:
0.92 (3H, t, J=7 Hz)
1.2-1.9 (2H, m)
2.5-2.8 (6H, m)
3.80 (3H, s)
3.8-4.0 (4H, m)
6.33 (1H, d, J=9 Hz)
7.00 (1H, d, J=9 Hz)

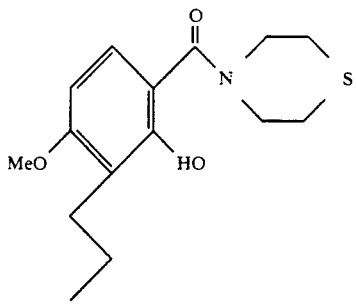 (XIV)

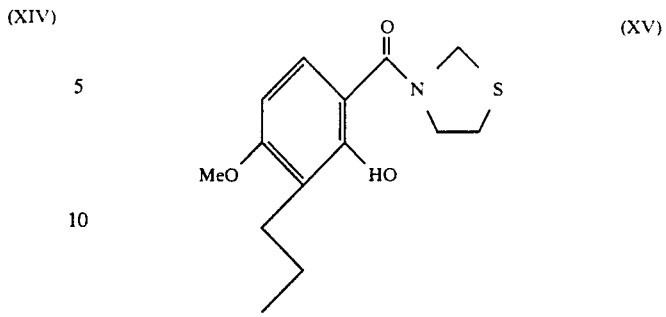 (XV)

EXAMPLE 3

Under argon atmosphere, a solution of 2-methoxymethoxy-3-n-propyl-4-methoxybenzoic acid (8 g) and 4-dimethylaminopyridine (0.38 g) in methylene chloride (150 ml) was cooled to 0° C., and to the solution was added N,N'-dicyclohexylcarbodiimide (7.8 g). The mixture was agitated for 15 minutes. Thiazolidine (3.0 ml) was added to the mixture, and the mixture was agitated at room temperature for another 15 hours. To the reaction mixture was added diethyl ether, and the mixture was filtered. Water and 1N aqueous hydrochloric acid were added to the filtrate, and the mixture was extracted with methylene chloride. The organic layer was washed with saturated aqueous solution of sodium bicarbonate, dried over anhydrous magnesium sulfate, and concentrated in evacuated atmosphere. The residue was subjected to column chromatography using silica gel. There was obtained N-(2-methoxymethoxy-3-n-propyl-4-methoxybenzoyl)thiazolidine (9.0 g) from fractions eluted with n-hexane-ethyl acetate (2:1).

The N-(2-methoxymethoxy-3-n-propyl-4-methoxybenzoyl)thiazolidine (9.0 g) was dissolved in a solution of methanol (100 ml)-water (20 ml). To the solution was added p-toluenesulfonic acid (2 spoonfuls in spatula) and the mixture was agitated at 60° C. for 23 hours. The reaction mixture was concentrated in evacuated atomosphere to about one fourth of the original volume. Saturated aqueous solution of sodium bicarbonate was added to the concentrate, and the mixture was extracted twice with ethyl acetate. The organic layer was washed with saturated aqueous solution of sodium chloride, dried over anhydrous magnesium sulfate, and concentrated in evacuated atomosphere. The residue was subjected to column chromatography using silica gel, and there was obtained N-(2-hydroxy-3-n-propyl-4-methoxybenzoyl)thiazolidine (7.3 g) from fractions eluted with n-hexane-ethyl acetate (5:1).

Data obtained from spectroscopic analysis of the product confirm the structure represented by the following formula (XV).

NMR (CDCl$_3$)δ:
0.92 (3H, t, J=7 Hz)
1.2-1.8 (2H, m)
2.64 (2H, t, J=7 Hz)
2.99 (2H, t, J=6 Hz)
3.81 (3H, s)
3.97 (2H, t, J=6 Hz)
4.73 (2H, s)
6.36 (1H, d, J=9 Hz)
7.20 (1H, d, J=9 Hz)

EXAMPLE 4

Under argon atmosphere, a solution of ethyl chlorocarbonate (7.65 ml) in methylene chloride (90 ml) was cooled to −15° C., and to the solution was added dropwise a solution of 2-hydroxy-3-n-propyl-4-methoxybenzoic acid (8 g) and triethylamine (11.1 ml) in methylene chloride (160 ml) for 30 minutes, and the mixture was agitated for another 15 minutes. 2-thiophenemethylamine (4.7 ml) was added to the mixture and the mixture was agitated for 3 hours while the temperature of the mixture was elevated to 0° C. The reaction mixture was poured into 1N aqueous hydrochloric acid, and extracted with methylene chloride. The organic layer was washed with a mixed solution of saturated aqueous solution of sodium chloride and saturated aqueous solution of sodium bicarbonate, dried over anhydrous magnesium sulfate, and concentrated in evacuated atomosphere. The residue was dissolve in methanol (100 ml), and the solution was cooled to 0° C. The solution was added to 8.5% aqueous solution of sodium hydroxide (50 ml) and the mixture was agitated at room temperature for 4.5 hours. The reaction mixture was acidified by adding 6N aqueous hydrochloric acid thereto, and extracted twice with ethyl acetate. The organic layer was washed with saturated aqueous solution of sodium chloride, dried over anhydrous magnesium sulfate, and concentrated in evacuated atomosphere. The residue was subjected to column chromatography using silica gel, and there was obtained N-(2-hydroxy-3-n-propyl-4-methoxybenzoyl)-2-thiophenemethylamine (5.7 g) from fractions eluted with n-hexane-methylene chloride (2:1).

Data obtained from spectroscopic analysis of the product confirm the structure represented by the following formula (XVI).

NMR (CDCl$_3$)δ:
0.92 (3H, t, J=7 Hz)
1.2-1.8 (2H, m)
2.64 (2H, t, J=7 Hz)
3.79 (3H, s)
4.71 (2H, d, J=6 Hz)
6.30 (1H, d, J=9 Hz)
6.8-7.3 (4H, m)

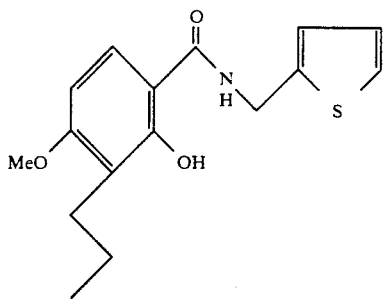 (XVI)

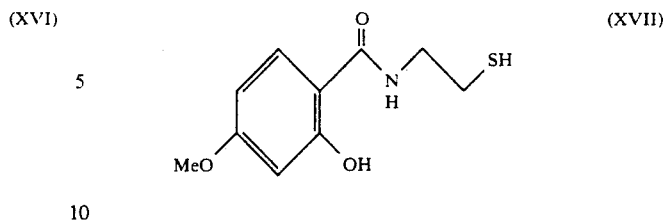 (XVII)

EXAMPLE 5

Under argon atmosphere, 2.84 g of 4-methoxysalicylic acid was dispersed in 45 ml of methylene chloride, and the dispersion was cooled to −15° C. To the dispersion was added 3.76 g of triethylamine and 3.77 g of ethyl chlorocarbonate, and the mixture was agitated for 1.5 hour. To the mixture was added a solution of 1.56 g of cysteamine in 5 ml of methylene chloride, and the mixture was agitated at −15° C. for 2 hours. The reaction mixture was poured into 1N aqueous hydrochloric acid, and extracted with methylene chloride. The organic layer was washed with saturated aqueous solution of sodium chloride, and dried over anhydrous sodium sulfate. The solvent was distilled off in evacuated atomosphere, and the residue was subjected to column chromatography using silica gel. There was obtained 4.50 g of N-(2-ethoxycarbonyloxy-4-methoxybenzoyl)-cysteamine.

4.50 g of the N-(2-ethoxycarbonyloxy-4-methoxybenzoyl)cysteamine was dissolved in 70 ml of methanol, and 17 ml of 2N aqueous solution of sodium hydroxide was added to the solution. The mixture was agitated for 45 minutes. The solvent was distilled off in evacuated atomosphere, and 2N aqueous solution of sodium hydroxide and methylene chloride were added to the mixture for separation. The aqueous phase was further washed with methylene chloride, acidified by adding 6N aqueous hydrochloric acid, and extracted with methylene chloride. The mixture was dried over anhydrous sodium sulfate, and the solvent was distilled off in evacuated atomosphere. The residue was subjected to column chromatography using silica gel, and there was obtained 2.63 g of N-(2-hydroxy-4-methoxybenzoyl)-cysteamine (I).

Data obtained from spectroscopic analysis of the product confirm the structure represented by the following formula (XVII).

NMR (CDCl$_3$)δ:
7.20 (1H, m)
6.60 (1H, br, S)
6.35 (3H, m)
3.75 (3H, s)
3.55 (2H, m)
2.70 (2H, m)
1.40 (1H, t)

EXAMPLE 6

Under argon atmosphere, a solution of ethyl chlorocarbonate (6.7 ml) in methylene chloride (80 ml) was cooled to −15° C., and to the solution was added dropwise a solution of 2-hydroxy-3-n-propyl-4-methoxybenzoic acid (7 g) and triethylamine (9.75 ml) in methylene chloride (140 ml) for 15 minutes, and the mixture was agitated for another 15 minutes. Cysteamine (5.64 g) was added to the mixture and the mixture was agitated at −15° C. for 1.5 hours. The reaction mixture was poured into 1N aqueous hydrochloric acid, and extracted with methylene chloride.

The organic layer was washed with saturated aqueous solution of sodium bicarbonate, dried over anhydrous magnesium sulfate, and concentrated in evacuated atmosphere. The residue was subjected to column chromatography using silica gel, and there was obtained N-(2-ethoxycarbonyloxy-3-n-propyl-4-methoxybenzoyl)cysteamine (6.4 g) from fractions eluted with n-hexane-ethyl acetate (2:1).

The N-(2-ethoxycarbonyloxy-3-n-propyl-4-methoxybenzoyl)cysteamine (6.4 g) was dissolved in methanol (50 ml), and the solution was cooled to 0° C. To the solution was added 15% aqueous solution of sodium hydroxide (10 ml), and the mixture was agitated at room temperature for 1.5 hours. The reaction mixture was acidified by adding 6N aqueous hydrochloric acid thereto, and concentrated to about one third of the original volume in evacuated atmosphere. The concentrate was extracted twice with ethyl acetate, and the organic layer was washed with saturated aqueous solution of sodium chloride, dried over anhydrous magnesium sulfate, and concentrated in evacuated atomosphere. The residue was subjected to column chromatography using silica gel, and there was obtained N-(2'-hydroxy-3'-n-propyl-4'-methoxybenzoylcysteamine (3.55 g) from fractions eluted with n-hexane-ethyl acetate (4:1 to 3:1).

Data obtained from spectroscopic analysis of the product confirm the structure represented by the following formula (XVIII).

NMR (CDCl$_3$)δ:
0.89 (3H, t, J=7 Hz)
1.2–1.7 (3H, m)
2.4–2.9 (4H, m)
3 3–3.7 (2H, m)
3.77 (3H, s)
6.30 (1H, d, J=9 Hz)
7.15 (1H, d, J=9 Hz)

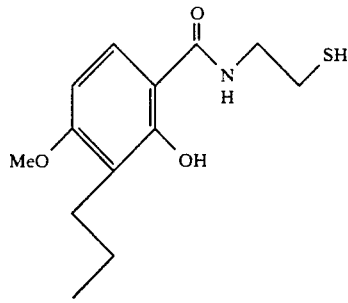

(XVIII)

EXAMPLE 7

7.90 g of phthaloylethyl-n-octylsulfide was dissolved in ml of ethanol, and 1.69 g of hydradine hydrate was added to the solution. After heating the mixture under reflux for 2 hours, the solvent was distilled off in evacuated atmosphere, and the residue was extracted with methylene chloride to produce 2-aminoethyl-n-octylsulfide.

In the meantime, 3.36 g of 4-methoxysalicylic acid was dispersed in 30 ml of methylene chloride under argon atmosphere, and the dispersion was cooled to −15° C. To the dispersion were added 4.47 g of triethylamine and 4.58 g of ethyl chlorocarbonate, and the mixture was agitated for 1.5 hours. To the mixture was added the 2-aminoethyl-n-octylsulfide which had been dissolved in 10 ml of methylene chloride, and the mixture was agitated at −15° C. for 2 hours. The reaction mixture was poured into 1N aqueous hydrochloric acid, and the mixture was extracted with methylene chloride. The organic layer was washed with saturated aqueous solution of sodium bicarbonate, and dried over anhydrous sodium sulfate. The solvent was distilled off in evacuated atmosphere, and the residue was subjected to column chromatography using silica gel. There was obtained 6.37 g of 2-(2'-ethoxycarbonyloxy-4'-methoxybenzoylamino)ethyl-n-octylsulfide, which was dissolved in 100 ml of methanol. To the solution was added 23 ml of 1N aqueous solution of sodium hydroxide, and the mixture was agitated for 35 minutes. The solvent was distilled off in evacuated atomosphere, and the residue was subjected to column chromatography using silica gel. There was obtained 3.55 g of 2-(2'-hydroxy-4'-methoxybenzoylamino)ethyl-n-octylsulfide.

Data obtained from spectroscopic analysis of the product confirm the structure represented by the following formula (XIX).

NMR (CDCl₃)δ:
11.15 (1H, br, S)
7.30 (1H, m)
6.75 (1H, br, S)
6.35 (2H, m)
3.75 (3H, s)
3.60 (2H, m)
2.60 (4H, m)
1.25 (15H, m)

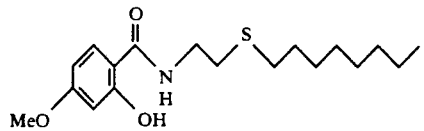

(XIX)

EXAMPLE 8

9.10 g of phthaloyl-n-octylsulfide was dissolved in 100 ml of ethanol, and 2.14 g of hydradine hydrate was added to the solution.

After heating the mixture under reflux for 3 hours, the solvent was distilled off in evacuated atomosphere to obtain a mixture of 2-aminoethyl-n-octylsulfide and hydrazide.

In the meantime, 6.00 g of 2-hydroxy-3-n-propyl-4-methoxy-benzoic acid was dispersed in 120 ml of methylene chloride, and the dispersion was cooled to −10° C. To the dispersion were added 9.93 ml of triethylamine and 5.45 ml of ethyl chlorocarbonate, and the mixture was agitated for 30 minutes. To the mixture was added the mixture of 2-aminoethyl-n-octylsulfide and hydrazide which had been dispersed in methylene chloride. The mixture was agitated at −10° C. to 0° C. for 3 hours. The reaction mixture was filtered, and the precipitate was washed with methylene chloride. The filtrate and the wash solution was combined, washed with water and then with saturated aqueous solution of sodium chloride, and dried over anhydrous sodium sulfate. The solvent was distilled off in evacuated atomosphere, and the residue was subjected to column chromatography using silica gel. There was obtained 6.28 g of 2-(2'-ethoxycarbonyloxy-3'-n-propyl-4'-methoxybenzoylamino)ethyl-n-octylsulfide.

3.86 g of the 2-(2'-ethoxycarbonyloxy-3'-n-propyl-4'-methoxybenzoylamino)ethyl-n-octylsulfide was dissolved in 60 ml of methanol, and 13 ml of 2N aqueous solution of sodium hydroxide was added to the solution. The mixture was agitated for 1 hour.

The solvent was distilled off in evacuated atomosphere, and the mixture was acidified with 1N aqueous hydrochloric acid, extracted with chloroform, and the extract was dried over anhydrous sodium sulfate. The solvent was distilled off in evacuated atomosphere and the residue was subjected to column chromatography using silica gel. There was obtained 2.10 g of 2-(2'-hydroxy-3'-n-propyl-4'-methoxybenzoylamino)ethyl-n-octylsulfide from fractions eluted with methylene chloride.

Data obtained from spectroscopic analysis of the product confirm the structure represented by the following formula (XX).

NMR (CDCl₃)δ:
7.13 (1H, d, J=9 Hz)
6.33 (1H, d, J=9 Hz)
3.77 (3H, s)
3.4–3.6 (2H, m)
2.3–2.8 (6H, m)
0.7–1.7 (20H, m)

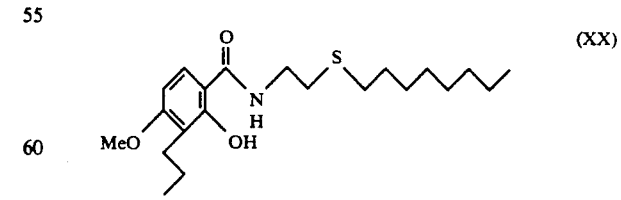

(XX)

EXPERIMENT 1

Effects for Suppressing Adjuvant Arthritis

The compounds according to the present invention obtained in the Examples were evaluated for their effects against adjuvant arthritis (diseased animal model for chronic articular rheumatism) of Lewis rats.

In the Experiment, five six week old male Lewis rats (body weight, 130 to 160 g) were treated as one group.

To right hind leg sole of rats from each group was subcutaneously injected with 0.2 mg of dry culture of Mycobacterium butyricum suspended in liquid paraffin. The compounds were suspended in 5% Tween 80, and the suspensions were orally administered to the rats once a day from the day next to the day of sensitization. The rats of both the medicated groups and the control group (non-medicated group) were intermittently measured for their volume of edema in their hind leg sole to examine the effects of the compounds for suppressing the adjuvant arthritis.

Percent increase in the volume of the hind leg sole due to the edema was calculated on the basis of the volume before sensitization, and suppression was determined by comparing the percent increase of the medicated group with that of the control group.

The results of 18 days after the sensitization are shown in Tables 1, 2 and 3.

TABLE 1

| Compound | Dose, (mg/kg) | Increase in volume due to edema | Suppression |
|---|---|---|---|
| XIII | 100 | 100.1 ± 3.1 | 23.5%*** |
| Control | — | 130.9 ± 5.1 | — |

TABLE 2

| Compound | Dose, (mg/kg) | Increase in volume due to edema | Suppression |
|---|---|---|---|
| XVII | 100 | 84.8 ± 10.4 | 38.4%* |
| Control | — | 137.6 ± 15.7 | — |

TABLE 3

| Compound | Dose, (mg/kg) | Increase in volume due to edema | Suppression |
|---|---|---|---|
| XIV | 100 | 102.8 ± 10.0 | 21.5%* |
| XV | 100 | 95.6 ± 9.6 | 27.0%* |
| XVI | 100 | 85.9 ± 11.1 | 34.4%** |
| XVIII | 100 | 91.6 ± 10.9 | 30.1%* |
| XIX | 100 | 76.8 ± 17.8 | 41.4%** |
| XX | 100 | 103.4 ± 8.8 | 21.1%* |
| Control | — | 131.0 ± 10.0 | — |

Note 1) The numbers of the compounds correspond to those indicated in the Examples.
Note 2) The symbols *, , *, and **** indicate significant differences in accordance with t-test, namely,
*P < 0.05;
**P < 0.02;
***P < 0.01;
****P < 0.001.

The above-described results reveal that the adjuvant arthritis of Lewis rats are suppressed by the compounds, and accordingly, that the compounds are provided with antirheumatic effects.

It was also confirmed that the compounds in accordance with the present invention whose results are not shown in Tables also exhibit similar effects.

ACUTE TOXICITY

Toxicity test was carried out by orally administering the compounds to ICR male mice (5 week old). $LD_{50}$ values for all of the compounds of the present invention were 1,000 mg/kg or more, confirming high safety in relation to the effectiveness.

INDUSTRIAL UTILITY

According to the present invention, there are provided a novel cysteamine derivative and an antirheumatic agent containing said cysteamine derivative.

The above-described compounds of the present invention suppress adjuvant arthritis, which is the diseased animal model for rheumatism. Therefore, the cysteamine derivative may be effectively used as an antirheumatic agent.

We claim:

1. A cysteamine derivative represented by general formula (I):

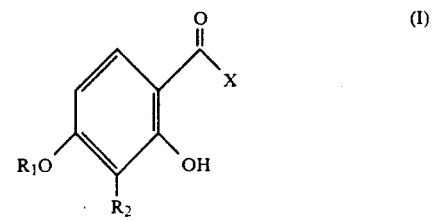

wherein $R_1$ represents a straight-chain or a branched alkyl radical having 1 to 6 carbon atoms, $R_2$ represents hydrogen atom or n-propyl radical, and X represents a radical selected from the group consisting of radicals containing cysteamine moiety (N∧S) represented by formula (II):

formula (III):

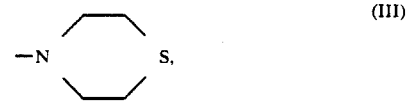

formula (IV):

formula (V):

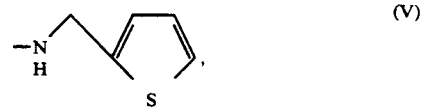

or formula (VI):

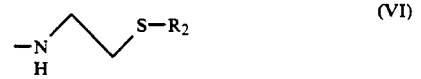

wherein $R_2$ represents hydrogen atom or a straight-chain or a branched alkyl group having 1 to 10 carbon atoms.

2. A cysteamine derivative according to claim 1, said cysteamine derivative being represented by general formula (VII):

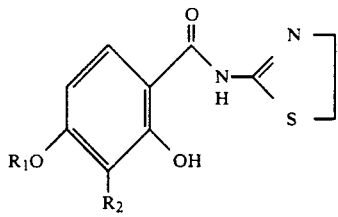
(VII)

3. A cysteamine derivative according to claim 1, said cysteamine derivative being represented by general formula (VIII):

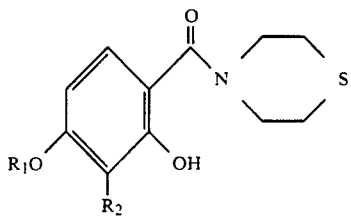
(VIII)

4. A cysteamine derivative according to claim 1, said cysteamine derivative being represented by general formula (IX):

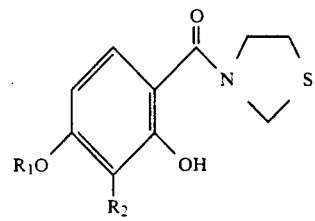
(IX)

5. A cysteamine derivative according to claim 1, said cysteamine derivative being represented by general formula (X):

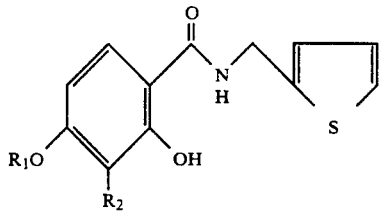
(X)

6. A cysteamine derivative according to claim 1, said cysteamine derivative being represented by general formula (XI):

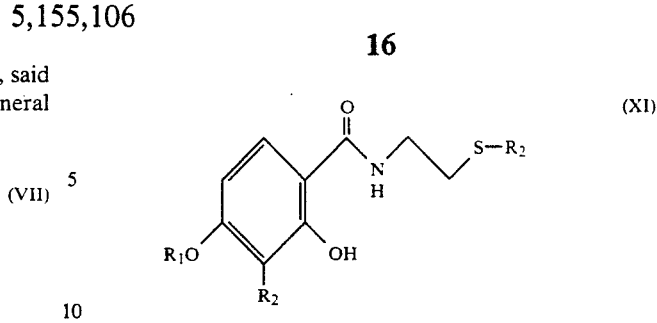
(XI)

7. An antirheumatic composition comprising an antirheumatically effective amount of the compound of claim 1 and a pharmaceutically acceptable carrier or vehicle.

8. An antirheumatic composition comprising an antirheumatically effective amount of the compound according to claim 2 and a pharmaceutically acceptable carrier or vehicle.

9. An antirheumatic composition comprising an antirheumatically effective amount of the compound according to claim 3 and a pharmaceutically acceptable carrier or vehicle.

10. An antirheumatic composition comprising an antirheumatically effective amount of the compound according to claim 4 and a pharmaceutically acceptable carrier or vehicle.

11. An antirheumatic composition comprising an antirheumatically effective amount of the compound according to claim 5 and a pharmaceutically acceptable carrier or vehicle.

12. An antirheumatic composition comprising an antirheumatically effective amount of the compound according to claim 6 and a pharmaceutically acceptable carrier or vehicle.

13. A method for treating rheumatism comprising, administering to an animal suffering from rheumatism an antirheumatically effective amount of a compound according to claim 1.

14. A method for treating rheumatism comprising administering an antirheumatically effective amount of a compound according to claim 2.

15. A method for treating rheumatism comprising administering to an animal suffering from rheumatism an antirheumatically effective amount of a compound according to claim 3.

16. A method for treating rheumatism comprising administering to an animal suffering from rheumatism an antirheumatically effective amount of a compound according to claim 4.

17. A method for treating rheumatism comprising administering to an animal suffering from rheumatism an antirheumatically effective amount of a compound according to claim 5.

18. A method for treating rheumatism comprising administering to an animal suffering from rheumatism an antirheumatically effective amount of a compound according to claim 6.

* * * * *